US00PP24042P3

(12) United States Plant Patent
Brown

(10) Patent No.: US PP24,042 P3
(45) Date of Patent: Nov. 26, 2013

(54) ***WESTRINGIA FRUTICOSA* PLANT NAMED 'NFL25'**

(50) Latin Name: *Westringia fruticosa*
Varietal Denomination: NFL25

(76) Inventor: Graham Brown, Pennant Hills (AU)

( * ) Notice: Subject to any disclaimer, the term of this patent is extended or adjusted under 35 U.S.C. 154(b) by 85 days.

(21) Appl. No.: 13/374,817

(22) Filed: Jan. 17, 2012

(65) Prior Publication Data

US 2013/0185836 P1 Jul. 18, 2013

(51) Int. Cl.
*A01H 5/00* (2006.01)

(52) U.S. Cl.
USPC ..... Plt./226

(58) Field of Classification Search
USPC ..... Plt./226
See application file for complete search history.

*Primary Examiner* — Susan McCormick Ewoldt
(74) *Attorney, Agent, or Firm* — Sam McCoy

(57) ABSTRACT

'NFL25' is a distinctive variety of *Westringia fruticosa* which is characterized by the combination of short plant height, decumbent growth habit, and large dark green leaves.

2 Drawing Sheets

Latin name of the genus and species: The Latin name of the genus and species of the novel variety disclosed herein is *Westringia fruticosa.*

Variety denomination: The inventive variety of *Westringia* disclosed herein has been given the variety denomination 'NFL25'.

BACKGROUND OF THE INVENTION

The present invention relates to a new and distinct perennial variety of *Westringia fruticosa*, which has been given the variety denomination of 'NFL25'. Its market class is that of an ornamental plant. 'NFL25' is intended for use in landscaping as a groundcover and in decorative containers.

Parentage: The *Westringia fruticosa* variety 'NFL25' was finally selected in 2009 in an Australian nursery in Cobbitty, New South Wales following a selection process carried out from 2005 to 2008 involving approximately 1000 seedlings of *Westringia fruticosa* 'WES05' (Australia PBR 2008/312, unpatented in the US) production stock. 'NFL25' is a seedling selection from open pollinated *Westringia fruticosa* 'WES05'. 'NFL25' was selected due to its short plant height, decumbent growth habit, and larger leaves.

Asexual Reproduction: 'NFL25' was first propagated asexually by division at a wholesale nursery in Richmond, New South Wales, Australia and has since been asexually propagated by division. The distinctive characteristics of the inventive 'NFL25' variety are stable from generation to generation; clones of the variety produced by asexual reproduction maintain the distinguishing characteristics of the original plant.

A Provisional Patent application for variety 'NFL25' was filed with the US Patent and Trademark Office on Jan. 21, 2010 under Application No. 61/461,614.

SUMMARY OF THE INVENTION

'NFL25' is a distinctive variety of *Westringia fruticosa* which is characterized by the combination of short plant height, decumbent growth habit, and large dark green leaves.

BOTANICAL DESCRIPTION OF THE PLANT

Figure 1:
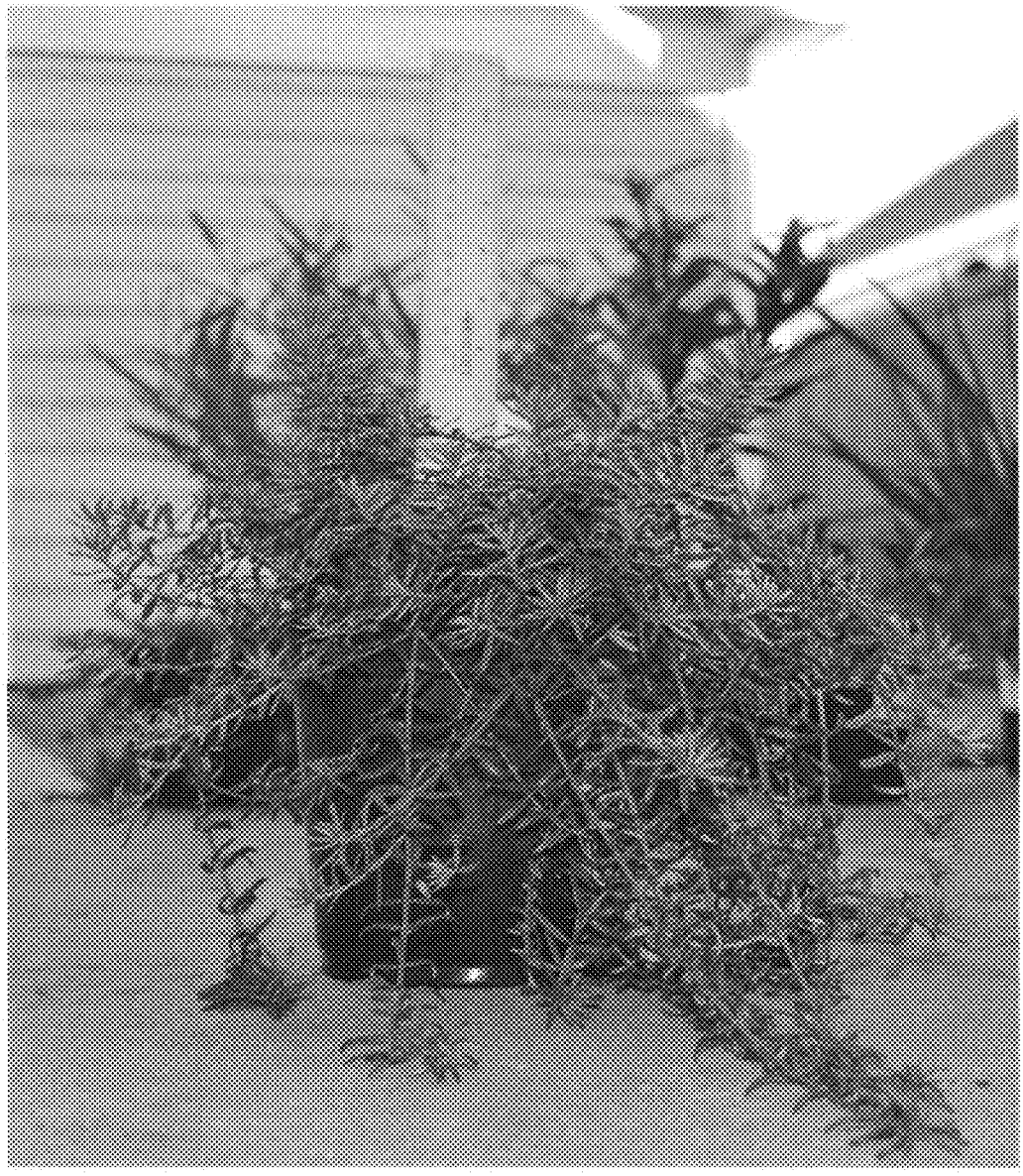
FIG. 1 shows a mature 1-gallon 'NFL25' plant, at 10 months old from a rooted cutting.
Figure 2:
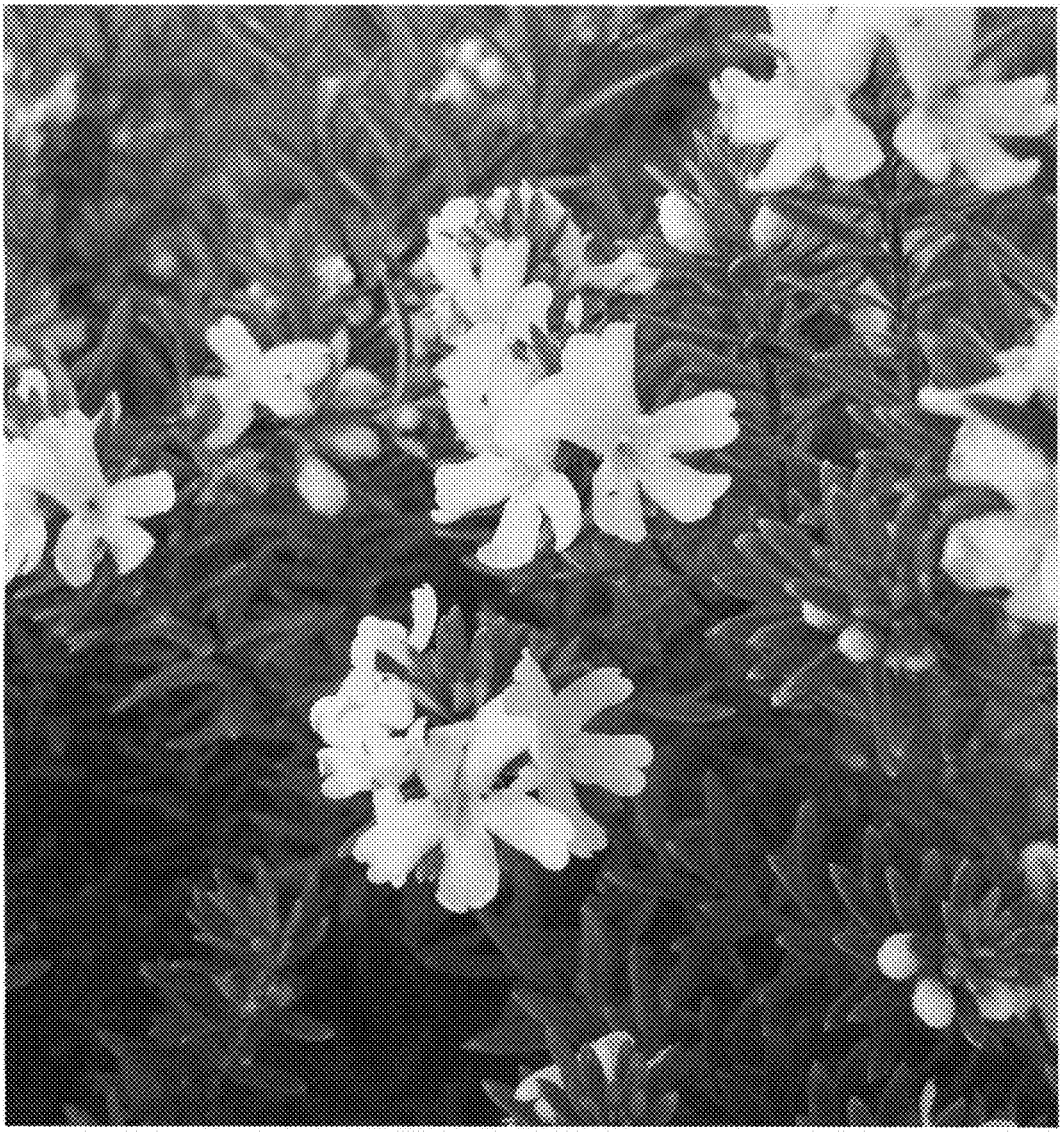
FIG. 2 shows a macro view of the 'NFL25' flower.

The following is a detailed botanical description of a new and distinct variety of a *Westringia fruticosa* ornamental plant known as 'NFL25'. Unless indicated otherwise, the flower and reproductive organ descriptions disclosed herein are based upon observations made in Clarendon, N.S.W. Australia in October 2010 of mature 'NFL25' plants grown in nursery pots. All other observations were made on plants grown in Charleston, S.C. Unless indicated otherwise, the descriptions disclosed herein are based upon observations made from mature 'NFL25' plants grown from rooted cuttings from April 2011 to December 2011 in trade 1-gallon nursery pots. Pots were filled with soilless potting media, maintained with granular slow release fertilizer, and manually watered as needed. No pest and disease measures were taken.

Those skilled in the art will appreciate that certain characteristics will vary with older or, conversely, younger plants. 'NFL25' has not been observed under all possible environmental conditions. Where dimensions, sizes, colors and other characteristics are given, it is to be understood that such characteristics are approximations or averages set forth as accurately as practicable. The phenotype of the variety may vary with variations in the environment such as season, temperature, light intensity, day length, cultural conditions and the like. Color notations are based on The Royal Horticultural Society Colour Chart, The Royal Horticultural Society, London, 1986 edition. Note that generic color descriptions such as 'white' do not exist in the R.H.S. charts and the corresponding R.H.S. colors are quoted.

'NFL25' is a perennial *Westringia fruticosa* plant which is a seedling selection from a *Westringia fruticosa* 'WES05'. 'NFL25' has large yellow-green leaves, a decumbent branching habit, short plant height and white flowers displayed within the foliage.

These features and other characteristics are apparent from the description provided below.

Growth Habit, Dimensions and Color

Plant description:

*Bloom period.*—Spring with sporadic flowering through summer and fall.

*Plant habit.*—Shrub; decumbent and dense.

*Height.*—17 cm to the tallest branch with the overall height of 13.5 cm.

*Width.*—58 cm.

*Hardiness.*—USDA Zone 9 to 11.

*Propagation.*—Propagation is accomplished using semi-hard wood cuttings. Roots well without rooting compound or hormone.

*Time to develop roots.*—Approximately 3 weeks.

*Crop time.*—From approximately three to four months are needed to produce a well rooted 1-gallon nursery pot, starting from a rooted cutting. Crop time varies with location and production practices.

*Pest and disease susceptibility or resistance.*—In common with the species, none of note.

*Environmental tolerances.*—Typical shade tolerance for the species. Excellent drought tolerance with moderate to good recovery from severe wilting if irrigated. Performs well in sandy soils, but also tolerates heavy, clay-type soils well.

Roots: The roots of 'NFL21' are colored white and fleshy and thick, similar to other *Westringia fruticosa.*

Stem:

*Shape.*—Cylindrical yet angular.

*Stem color.*—Young stem is closest to yellow green 144A to 144B.

*Stem dimensions.*—The longest of any mature stems is approximately 45 to 50 cm in length with a diameter of 7 to 9 mm near the base.

*Stem surface.*—Corky and pruinose.

*Basal stem color.*—Brown 200A with grey brown (RHS 199D) striations at maturity.

*Branching and habit.*—Strong branching habit; decumbent.

*Internode length.*—Average of 20.5 mm. However, there appears to be a positional effect whereby internodes near the plants base are much shorter (average of 7.5 mm) than the internodes on the longest outstretching stems which average 17.25 mm.

Foliage:

*Type.*—Evergreen.

*Shape.*—Elliptical, narrow.

*Division.*—Simple.

*Apex.*—Acute.

*Base.*—Cunneate.

*Venation.*—Pinnate.

*Vein color.*—Indistinguishable from lamina, from both the adaxial and abaxial aspect.

*Margins.*—Entire.

*Arrangement.*—Whorled.

*Attachment.*—Petiolate.

*Texture.*—Leathery.

*Surfaces* (*adaxial surface*).—Lightly pubescent.

*Surfaces* (*abaxial surface*).—Heavily pubescent.

*Mature leaf dimensions.*—Average length of 19.9 mm, width is 4.1 mm on average.

*Leaf color* (*adaxial surface*).—Juvenile: yellow green 146A; mature: yellow green 147A.

*Leaf color* (*abaxial surface*).—Juvenile: green white 157A; mature: green white 157A.

*Petiole.*—Approximately 2.5 mm in length; width is less than 1 mm.

*Stipules.*—Laminar and green (RHS 138A); pubescent; length is approximately 3 mm.

Inflorescence: None; flowers are sessile.

Bud: Obovoid in shape and rounded at the apex. Approximately 6 mm long and 3 mm wide prior to dehiscence. Color is violet 157B.

Flowers: Flowers are sessile, singular and persist for approximately 5 days. Self cleaning. Non fragrant. Sympetalous, irregular with sepal lobes appearing to number four, width across the corolla measuring 14 to 15 mm and a length of 20 to 21 mm from base of sepal to apex of petal; color approximates to white RHS 155C. Calyx is synsepalous with five lobes; apex is acute; color is green (RHS 137C).

Reproductive organs:

*Stamens.*—4.

*Stamen color.*—155C.

*Stamen dimensions.*—About 3 mm in length and very thin.

*Attachment.*—Each stamen joins floral tube independently: Free.

*Anther dimensions.*—Minute.

*Anther color.*—Yellow.

*Pollen.*—Absent.

*Pistil.*—One.

*Pistil dimensions.*—About 8 mm. in length and very thin.

*Pistil color.*—155C.

*Ovary position.*—Half-Inferior.

Fruit and seed production: Not yet observed.

Comparison of NFL25 with Other Varieties of *Westringia fruticosa*

'NFL25' is similar to the parent *Westringia fruticosa* 'WES05' in that both have dark green elliptical leaves and a relatively small stature by comparison to the species, *Westringia fruticosa* common form. However 'NFL25' has a shorter plant height and decumbent branching which creates a low and spreading growth habit whereas 'WES05' is taller and has a bushy habit. 'NFL25' is a short plant measuring 16.7 cm tall in container grown trials whereas 'WES05' plants of similar age and container size reach 29.3 cm tall. The leaves of 'NFL25' are also larger than those of 'WES05'. The leaves of 'NFL25' measure 19.9 mm long and 4.1 mm wide, on average, whereas the leaves of 'WES05' have an average length and width of 17.2 mm and 3.1 mm, respectively.

'NFL25' is similar in size and habit to *Westringia fruticosa* 'White Rambler' (not patented) however 'NFL25' has darker green leaves, shorter plant height and larger leaves. 'NFL25' plants measure 16.7 cm tall whereas 'White Rambler' plants of similar age measure 21.4 cm tall. 'NFL25' has elliptical leaves that are an average length of 19.9 mm and an average width of 4.1 mm whereas the leaves of 'White Rambler' are linear and measure 16.6 mm long and 2.4 mm wide. The leaves of 'NFL25' are a darker shade of yellow green. 'NFL25' has foliage that is yellow green 147A whereas the foliage color of 'White Rambler' is yellow green 146B.

The combination of its short plant height, decumbent habit and large dark green leaves makes 'NFL25' a desirable ornamental plant suited for mass production for pot and landscape use.

That which is claimed is:

1. A new and distinct variety of *Westringia fruticosa* plant named 'NFL25', substantially as described and illustrated herein.

* * * * *